US008329477B2

(12) United States Patent
Groepler

(10) Patent No.: US 8,329,477 B2
(45) Date of Patent: Dec. 11, 2012

(54) METHOD AND SYSTEM FOR CONTROLLABLY RELEASING SOLUTIONS

(76) Inventor: Paul F. Groepler, Austin, TX (US)

( * ) Notice: Subject to any disclaimer, the term of this patent is extended or adjusted under 35 U.S.C. 154(b) by 1618 days.

(21) Appl. No.: 11/392,160

(22) Filed: Mar. 29, 2006

(65) Prior Publication Data

US 2006/0223196 A1 Oct. 5, 2006

Related U.S. Application Data

(60) Provisional application No. 60/666,656, filed on Mar. 30, 2005, provisional application No. 60/740,374, filed on Nov. 29, 2005.

(51) Int. Cl.

| | |
|---|---|
| ***G01N 33/543*** | (2006.01) |
| ***G01N 33/53*** | (2006.01) |
| ***G01N 33/50*** | (2006.01) |
| ***G01N 33/00*** | (2006.01) |

(52) U.S. Cl. ......... 436/518; 422/50; 422/68.1; 422/500; 428/221; 428/292.1; 428/293.4

(58) Field of Classification Search .................. 422/103, 422/50, 68.1, 500; 428/319.3, 304.4, 221, 428/292.1, 293.4; 506/32; 436/518

See application file for complete search history.

(56) References Cited

U.S. PATENT DOCUMENTS 7,094,464 B2 * 8/2006 Mao et al. .................. 428/319.3
2003/0124332 A1 * 7/2003 Mao et al. .................. 428/304.4

FOREIGN PATENT DOCUMENTS

WO WO 03/020425 * 3/2003

* cited by examiner

*Primary Examiner* — Christine T Mui

(74) *Attorney, Agent, or Firm* — William D. Wiese; DuBois, Bryant & Campbell, LLP

(57) ABSTRACT

A method and system for releasing active ingredients into the surrounding atmosphere is disclosed. In one embodiment, the dispersion rate of the active ingredient through the membrane is passively regulated by adjusting the porosity of the membrane. In another embodiment, materials with microfluidic channels of various diameters are interposed together so that the configuration of the channels approximates a venturi, thereby improving the flow of the solution through the microfluidic channels. In another embodiment, heat is applied to the top membrane layer to further accelerate the rate at which fluid is dissipated through the membrane structure. Devices incorporating membranes with the disclosed properties are also presented.

2 Claims, 13 Drawing Sheets

530

520

510

METHOD AND SYSTEM FOR CONTROLLABLY RELEASING SOLUTIONS

CROSS REFERENCE TO RELATED APPLICATION

This non-provisional application claims priority based upon prior U.S. Provisional Patent Application Ser. No. 60/666,656 filed Mar. 30, 2005 in the name of Paul F. Groepler, entitled "Devices with Changeable Scent," and U.S. Provisional Patent Application Ser. No. 60/740,374 filed Nov. 29, 2005 in the name of Paul F. Groepler, entitled "Devices with Changeable Scent," the disclosures of which are fully incorporated herein by reference.

FIELD OF THE INVENTION

The present invention relates to a method and system for dispersing a liquid, and more particularly, to a method and system for controllably releasing an active ingredient combined with a carrier into the surrounding atmosphere.

BACKGROUND

Devices for dispersing a liquid such as, for example, air freshening device in which there is a slow release of vapor into air from a liquid are well known in the art. However, such devices typically rely on passive evaporation of the liquid from a wick. Most commonly, one end of a wick is placed in a fluid to be dispersed, while the other end is exposed to the atmosphere. Capillary action forces liquid through the wick and up to the exposed end, where the liquid evaporates from the end of the wick and into the surrounding atmosphere. These devices are generally known to have the disadvantages of dispersing the liquid at an uneven rate and composition. For example, the more volatile components of the liquid mixture will evaporate faster thereby leaving an increasingly greater percentage of the less-volatile components in the remaining composition.

Devices for spraying liquid into the surrounding atmosphere using electrostatic force are also well known in the art. In these devices, the liquid is typically delivered to the point of high electric potential through, for example, capillary rise in a small diameter tube. The liquid is drawn out by electrostatic forces into ligaments which break up into fine droplets. While these devices can be effective under certain circumstances, such as when the transfer of liquid greatly exceeds the evaporation rate, they typically require relatively high voltage to operate properly and can be somewhat fragile.

Still other devices are known which employ gravitational forces to diffuse liquid through a membrane. One side of a membrane is exposed to liquid and the other side is exposed to the atmosphere. The liquid diffuses through the membrane and volatilizes into the surrounding atmosphere from the exposed surface of the membrane at a rate dependent on the porosity of the membrane.

While the foregoing controlled delivery systems sufficiently disperse liquids for some applications, they fail to provide a controlled, steady release of liquid over an extended period of time. More specifically, they do not disperse the active ingredient consistently over time. They also fail to adequately disperse non-volatile liquids, liquids of higher viscosity and gels.

There is a need, therefore, for a device for consistently dispersing liquid over time, that is easy to use and inexpensive to manufacture.

BRIEF SUMMARY OF THE INVENTION

The present invention is an improved method and system for controllably releasing an active ingredient combined with a carrier, also called a base, into the surrounding atmosphere. In one embodiment, the dispersion rate of the active ingredient through the membrane is passively regulated by adjusting the carrier and the porosity of the membrane. In another embodiment, materials with microfluidic channels of various diameters are interposed together so that the configuration of the channels approximates a venturi, thereby improving the flow of the solution through the microfluidic channels. In another embodiment, heat is applied to the top membrane layer to further accelerate the rate at which fluid is dissipated through the membrane structure.

These features and advantages, as well as others, will be apparent from the following more detailed description of the preferred embodiments of the invention, as illustrated in the accompanying drawings.

BRIEF DESCRIPTION OF THE DRAWINGS

A better understanding of the system and method of the present invention may be had by reference to the drawings, wherein.

DETAILED DESCRIPTION

Figure 1:
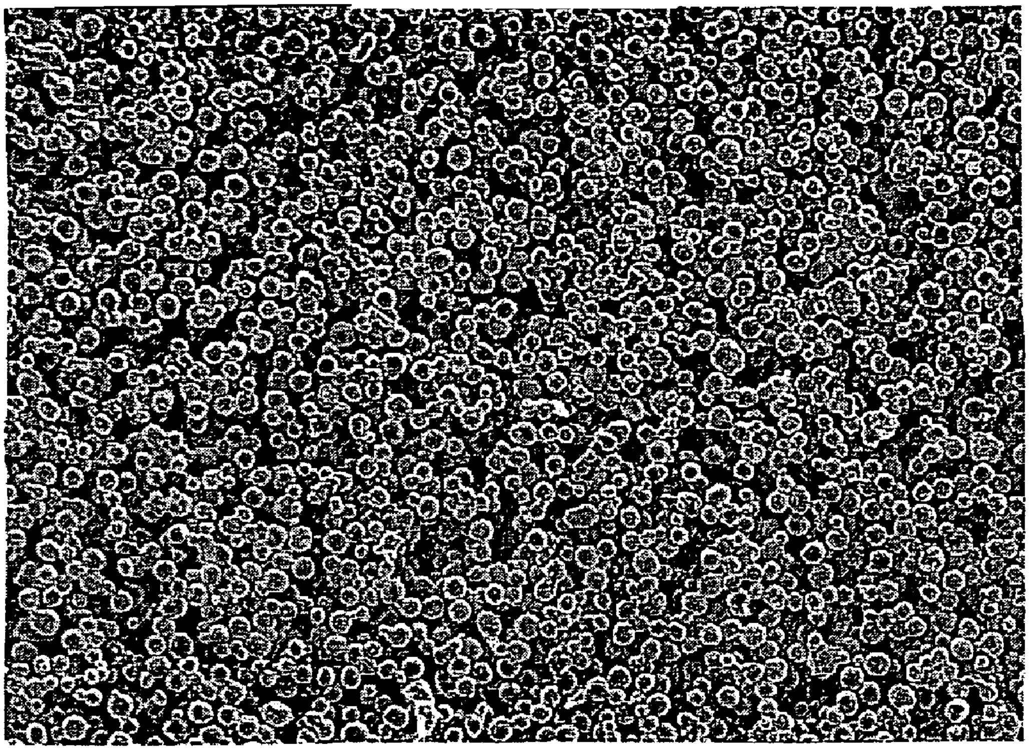
FIG. 1 shows a porous membrane manufactured with beads of predefined geometry.

This invention relates to method and system for dispersing solutions. While the invention is applicable to the release of all kinds of liquid or gaseous solutions, it is particularly concerned with the dispersal of solutions containing an active ingredient, such as a fragrance, into the surrounding atmosphere. As noted above, continuous dispersal is desirable in certain applications, such as for modulating or controlling the release of a fragrance. The present invention provides methods of achieving continuous dispersion and/or regulating or modulating dispersion rates through a membrane, such as changing the flow rate by adjusting the porosity of the membrane.

The invention may be used in connection with the dispersion of solutions from any source. Accordingly, the "liquid reservoir" described herein may be substituted for a removable reservoir, a disposable pad, a saturated foam or any other apparatus for retaining a solution. In certain embodiments, the liquid reservoir may be provided prefilled with a solution for a single use. In other embodiments, the liquid reservoir may include a refilling port which will enable a user to refill and reuse the device.

"Active ingredient" may be, for example, any one or more of perfumes, parasiticides, insect repellants, air fragrances, medicines, greases and pastes and combinations thereof, in liquid and/or gel form and in varying viscosities. The active ingredient may be dispersed in the solution in the form of particles, reagents or the like.

The active ingredient is dispersed in a liquid to form a solution. The liquid is often referred to as a "carrier," a "base" or a "solvent" and, unless otherwise specified, these terms are used interchangeably herein.

"Membrane" refers to a plastic material that is full of holes or pores, or that is capable of absorbing moisture, or which is permeable by liquids. These materials include, but are not limited to, a polyethylene material, a polypropylene material, a high molecular weight polyethylene material, a polyvinylidene fluoride material, an ethylene-vinyl acetate material, a polytetrafluoroethylene material, a stryene-acrylonitrile material, a polysulfone material, a polycarbonate material, and a polyhthalate material.

This present invention provides a method for controllably dispersing a solution from a liquid reservoir through a semi-permeable membrane into the surrounding atmosphere. In one embodiment, a material is passively placed in contact with a liquid comprising a carrier and an active ingredient wherein, due to the configuration of the material, the liquid passes through the material in such a manner that the active ingredient is consistently dispersed in to the surrounding atmosphere over time. In another embodiment, materials with varying micro-capillary openings are interfaced with one another and a voltage differential is create a across the layers so as to create a venturi effect, thereby actively propelling the liquid into the surrounding atmosphere. In yet another embodiment, the present invention provides a solution dispersal system that includes the aforementioned liquid reservoir, solution and membrane all mounted in a device. The device comprises a delivery system for the active ingredient.

First addressing the method and system for passively dispersing liquids. In this embodiment, a solution containing an active ingredient passes through a membrane in such a manner that the active ingredient is evenly disbursed over time. In this embodiment, the active ingredient may be one or more of perfumes, parasiticides, insect repellants, air fragrances, medicines, greases and pastes and combinations thereof, in liquid and/or gel form and in varying viscosities. A carrier, or "base," is combined with the active ingredient to form the solution. The carrier can be water, organic solvents or a combination thereof as required in order to control the diffusion of the solution through the membrane. Suitable solvents include the lower alcohols like ethyl alcohol and isopropyl alcohol; glycol ethers, 2-butoxyethanol, ethylene glycol monoethyl ether, propylene glycol and diethylene glycol monoethyl ether or monomethyl ether and mixtures thereof. Also, non-aqueous solvents can be present in the conditioning composition of the present invention if required to facilitate or impede diffusion, as desired.

Figure 10:
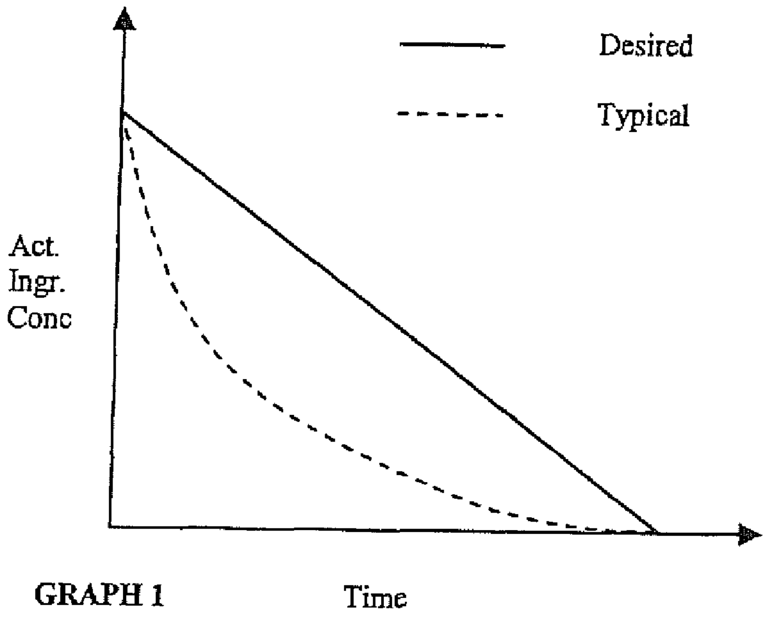
FIG. 10 shows a graph of the dispersion of a liquid over time.

One novel aspect of the present invention is the combination of the membrane with a liquid to create a dispersion effect that allows for the controlled release of the liquid. Ideally, when the strength of the active ingredient is plotted on a graph over time, the active ingredient would be dispersed linearly as shown in FIG. 10.

The membrane used to control the flow of the liquid may be any of a variety of materials. For example, the membrane may comprise an open cell material such as a polytetrafluoroethylene (PTFE) matrix material commercially available from Porex Technologies, Farburn, Ga. These materials are typically comprised of a bed of small polymeric particles that have been fused, or sintered, together by heat and pressure to form a porous membrane of predefined geometry such as shown in FIG. 1. Preferably, such an open cell material has a pore size in the range from about 1 micron to about 500 microns, and more preferably between about 5 and 50 microns. Various other plastic materials may also be used to construct the open cell matrix, including polyethylene (HDPE), ultra-high molecular weight polyethylene (UHMW), polypropylene (PP), polyvinylidene fluoride (PVDF), nylon 6 (N6), polyethersulfone (PES), ethyl vinyl acetate (EVA), and the like. Alternatively, the support structure may be constructed of a woven synthetic material, a metal screen, a stack of solid glass or plastic beads, and the like.

The membrane is placed in contact with a solution in a reservoir wherein a first side of the membrane is exposed to the solution and the opposite side of the membrane is exposed to the atmosphere. The solution diffuses through the membrane at a rate dependent on the membrane's porosity. The solution then evaporates off of the side of the membrane that is exposed to the atmosphere.

Table 1 shows the results of an experiment in which the strength of a fragrance as the active ingredient in a solution was measured over time. Each of the materials was dosed with 10 microliters of Givaudan product "Chai Tea" UM045969/00 fragrance oil and base; Lot #CU00004549. The strength measurement is a measure of the relative strength of the scent after the designated period of time, with the original scent received from Givaudan being the 100% baseline.

TABLE 1

| Material Type | 1 Month Result | 3 Month Result | 8 Month Result | 10 Month Result |
|---|---|---|---|---|
| Porex 4904 | 90% | 70% | 40% | 1% |
| Porex 4741 | 100% | 90% | 50% | 5% |
| Porex 4901 | 90% | 70% | 50% | 1% |
| Porex 4925 | 100% | 100% | 80% | 15% |
| Porex 353007 | 80% | 60% | 40% | 0% |
| Porex 4898 | 100% | 90% | 70% | 5% |
| Porex HWS | 90% | 90% | 70% | 5% |
| Porex LB | 80% | 80% | 50% | 0% |
| Porex MS | 80% | 70% | 40% | 1% |

As can be expected, the best result was obtained using Porex product number 4925, a 0.125 inch thick polyethylene material with an average pore size of 15 to 40 microns. Other materials such as Porex product number 4904, a 0.125 inch thick polyethylene material with a average pore size of 50 to 90 microns, allowed the active ingredient to escape more rapidly.

There are times when a passive dispersion system, such as that described above in which an active ingredient, such as a fragrance, is dispersed into the atmosphere when a container is opened, adequately disperses the active ingredient. However, in other instances, such a delivery system is insufficient to transmit the volume of active ingredient desired. In such cases, it may be desirable or necessary to utilize an active dispersion system.

In another embodiment of the present invention, membranes with microfluidic channels of various diameters are interposed together so that the configuration of the channels approximates a venturi, thereby improving the flow of the solution through the microfluidic channels. Once again, the solution consists of an active ingredient, such as a perfume, parasiticide, insect repellant, air fragrance, or medicine or any combination thereof, in liquid and/or gel form and in varying viscosities and a carrier.

Figure 2:
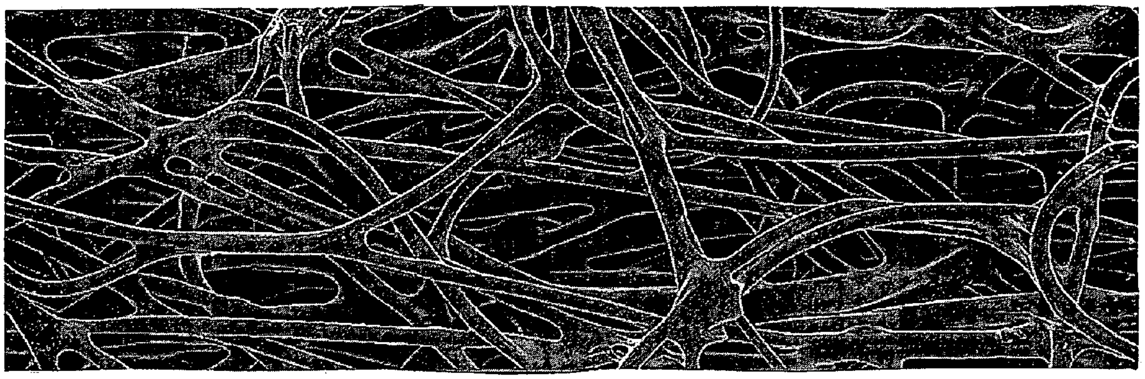
FIG. 2 shows a membrane comprised of a tubular structure.

In this embodiment, a series of membranes with microfluidic channels are placed in contact with one another in a configuration which approximates a tube with a constriction in the middle, also called a venturi. These materials are typically comprised of polymeric materials with tubular structures such as shown in FIG. 2.

Figure 3:
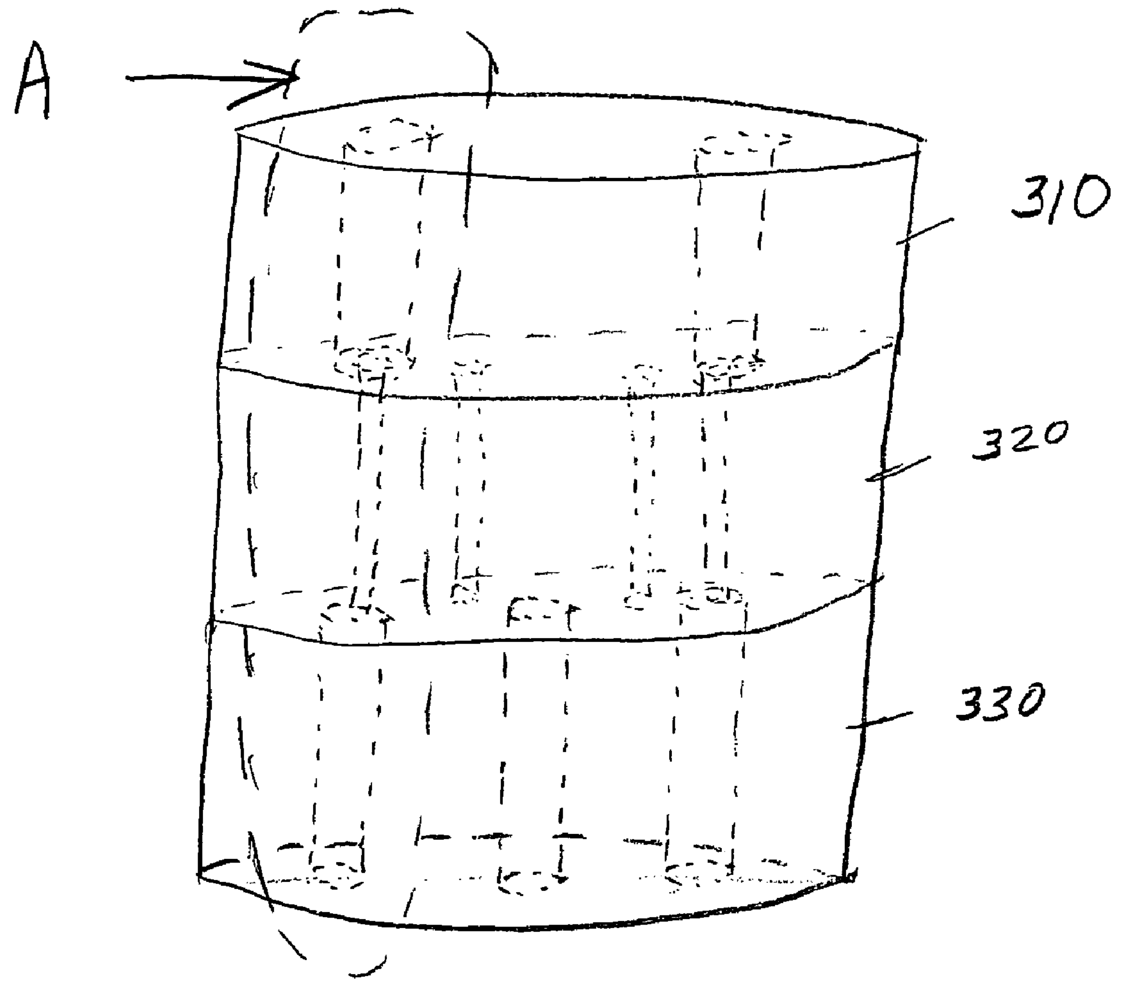
FIG. 3 shows one embodiment of the current invention in which three membranes are interposed upon one another to approximate a venturi configuration.

As few as three membranes may be placed together to approximate a venturi using the configuration shown in FIG. 3. A first membrane 310 contains microfluidic channels of predetermined cross-sectional areas so as to permit a certain level of maximum flow therethrough. The structure of the membranes described herein can take a variety of shapes and conformations, provided the structure includes at least one microfluidic channel element disposed within it. In some cases the microfluidic channels have a tubular configuration, much like a capillary, which may have internal diameters in the micron range. Alternatively, membrane structures may incorporate non-uniform shapes and/or conformations, depending upon the application for which the membrane configuration is to be used. For example, although the microfluidic channels are shown in the figure as being straight, in alternate embodiments they comprise a tortuous path such as a helical configuration, although other configurations, such as sinusoidal paths are likewise contemplated.

Figure 4:
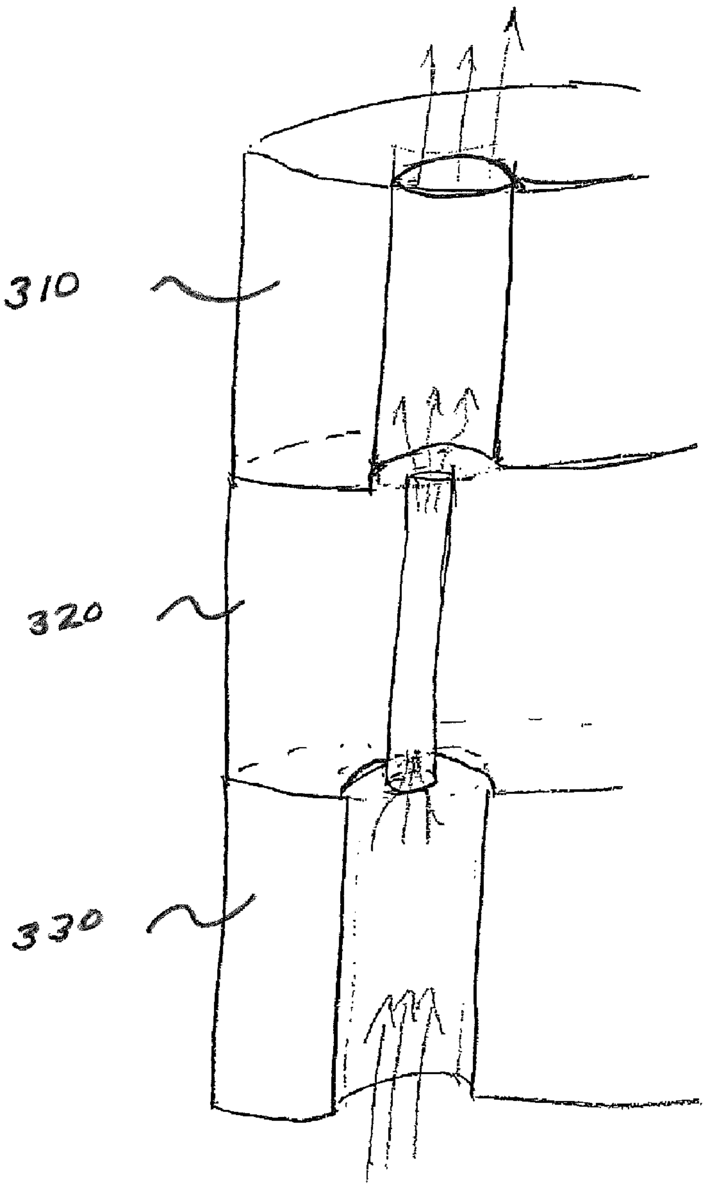
FIG. 4 shows a cross-section of the configuration depicted in FIG. 3.
Figure 5A:
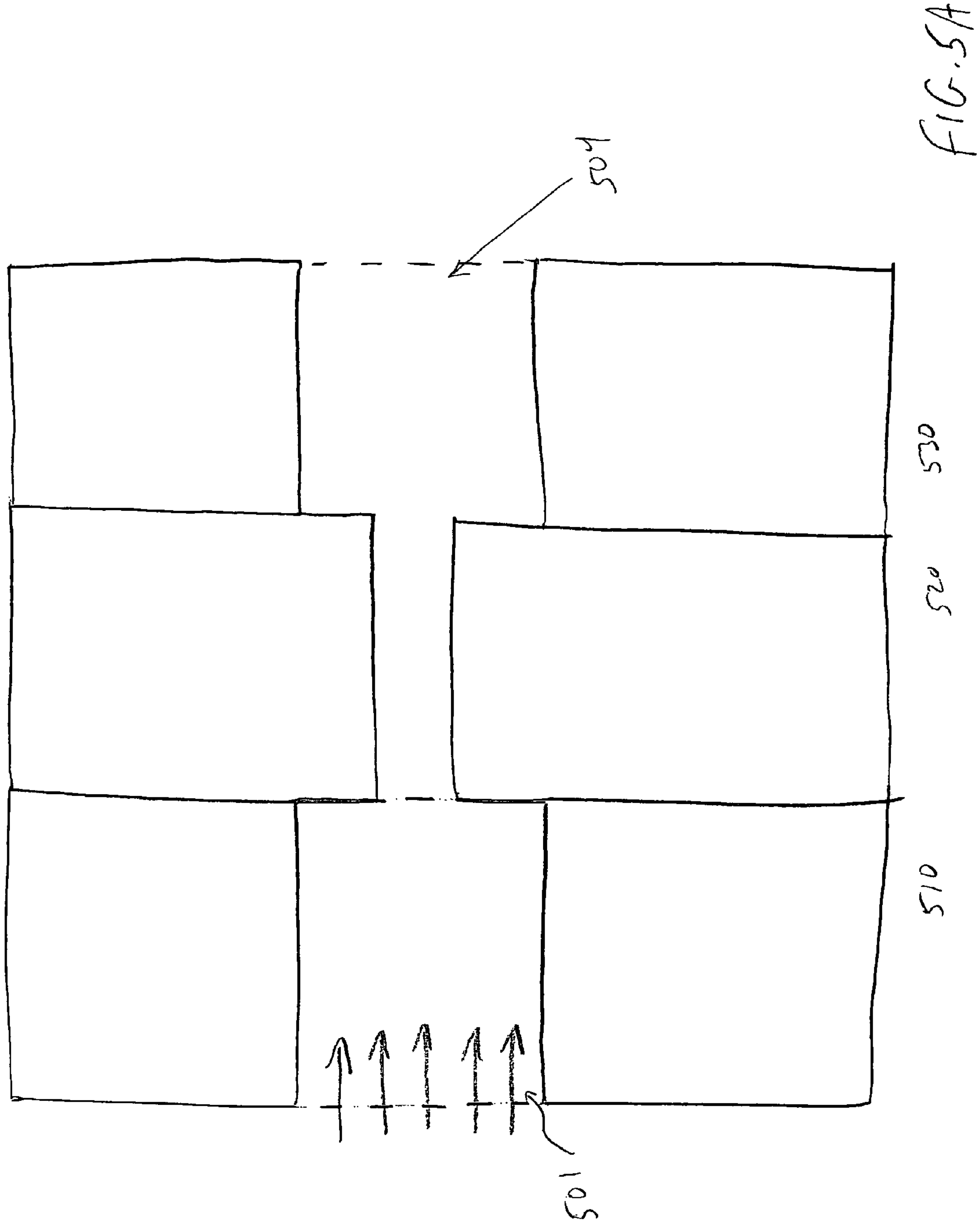
FIGS. 5A-5D show a sequential diagrammatic depiction of the air flow giving rise to the venturi effect.
Figure 5B:
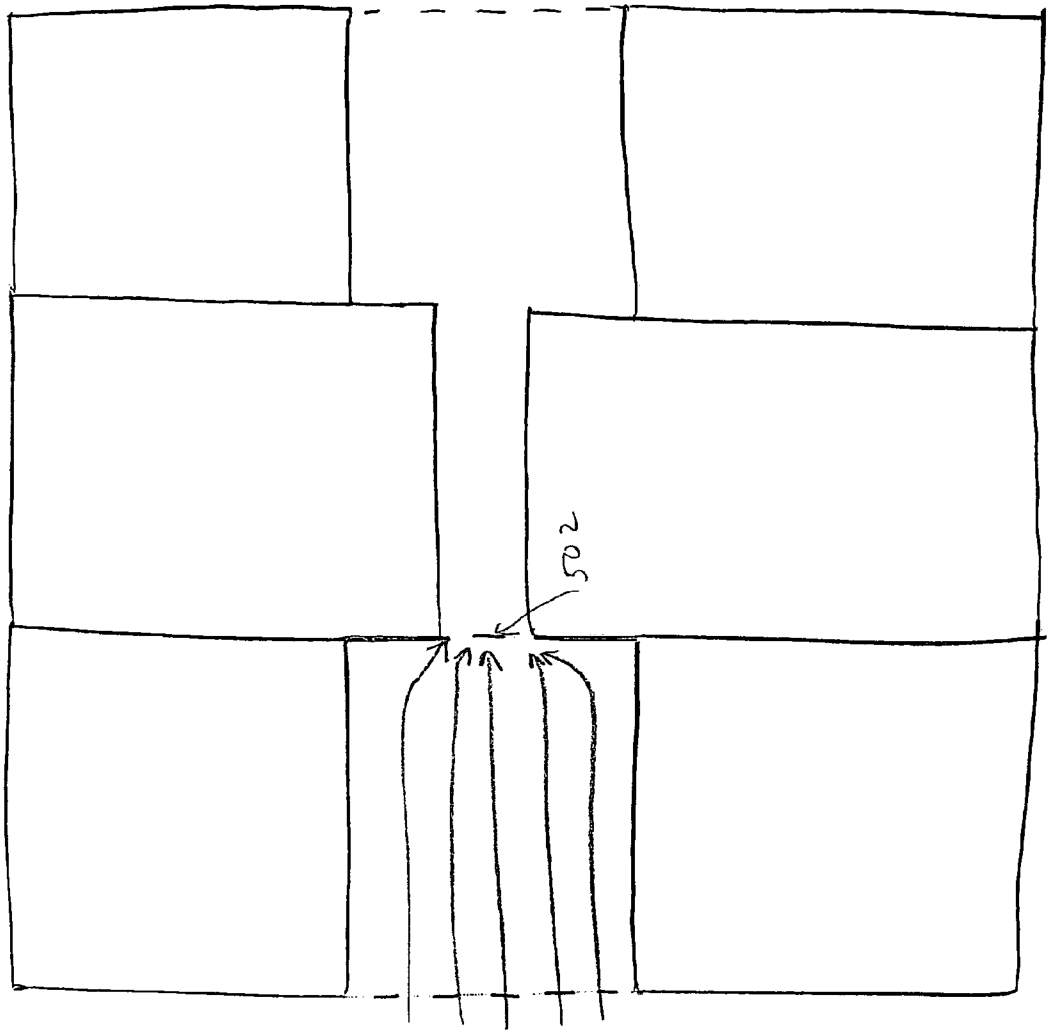
Figure 5C:
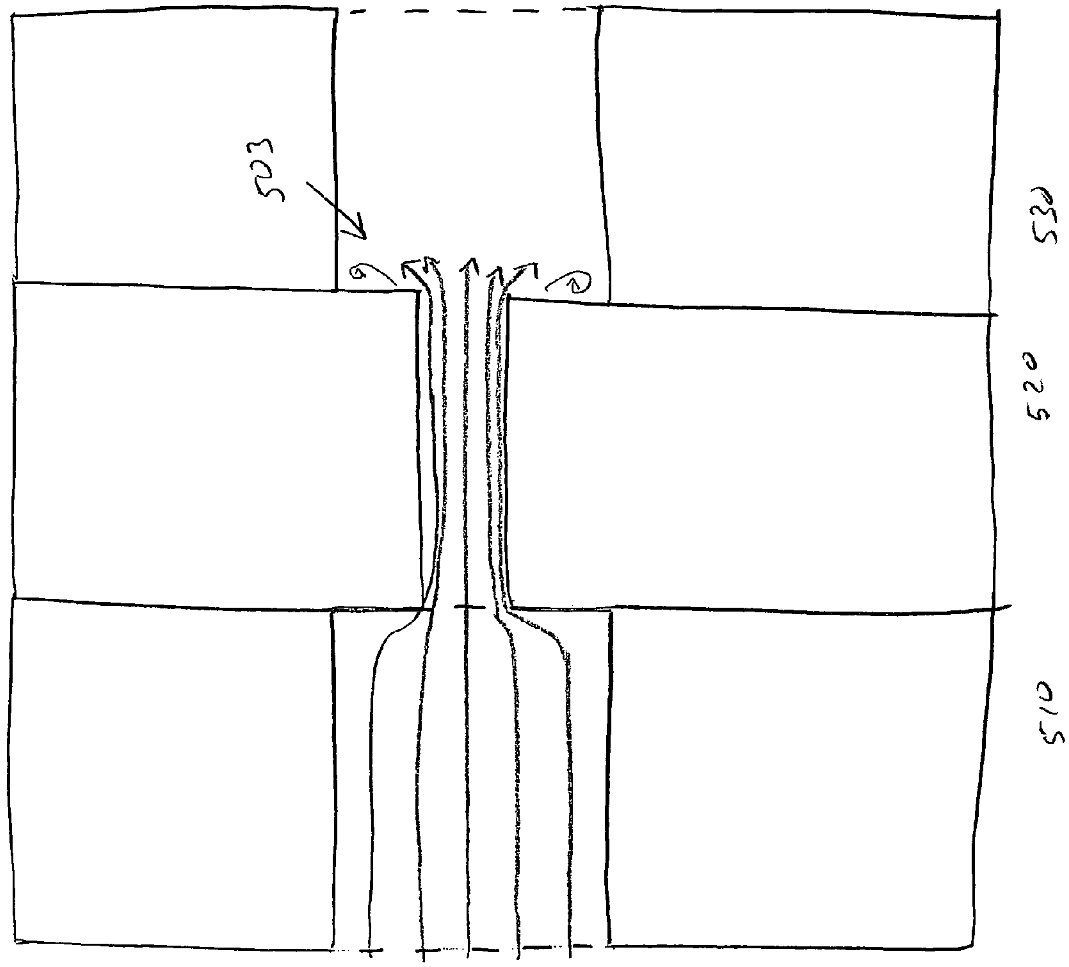
Figure 5D:
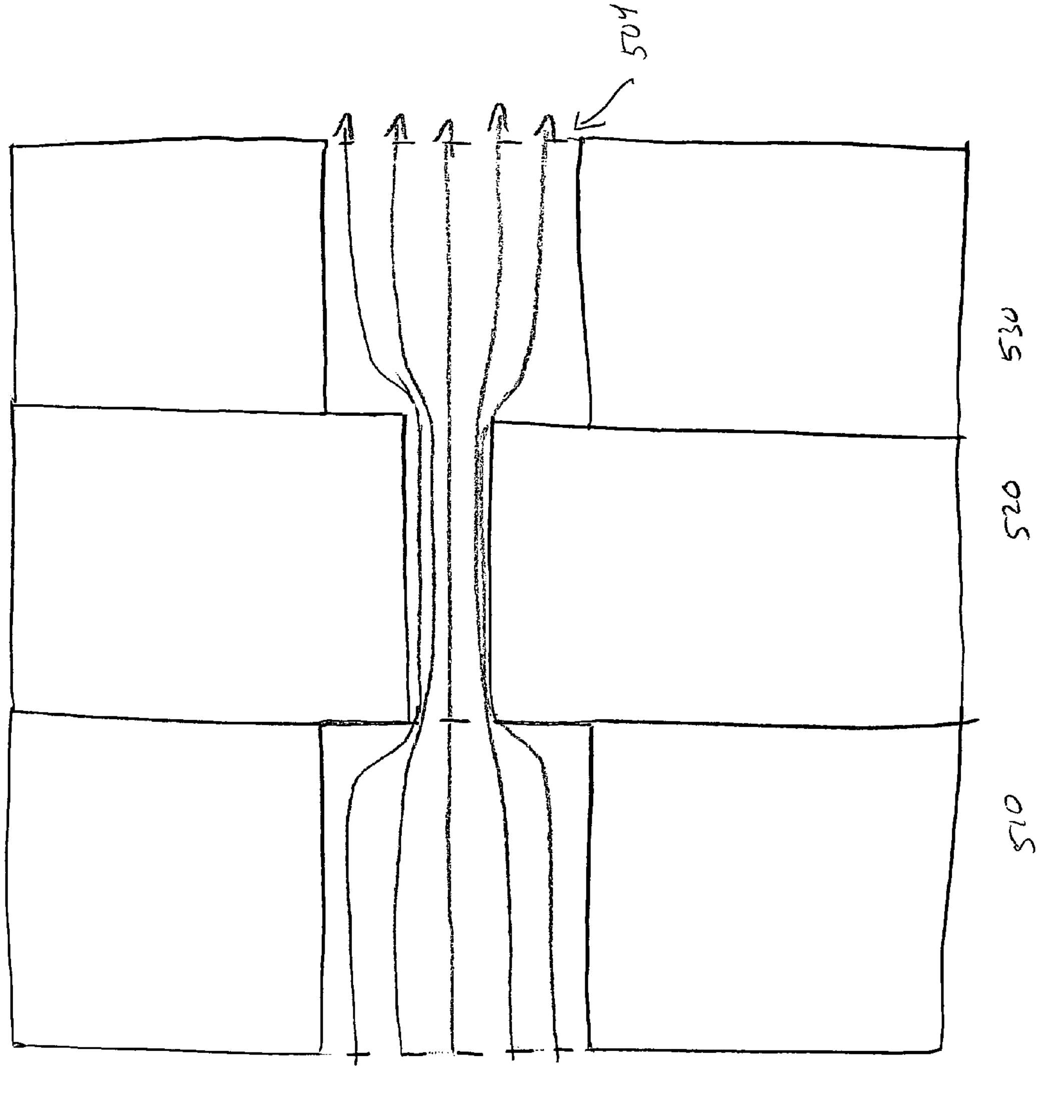

Referring now to FIG. 4, a first surface of a second membrane 320 containing microfluidic channels is placed in contact with the first membrane 310. The microfluidic channels of the second membrane 320 are smaller in diameter than the microfluidic channels of the first membrane 310. Although the openings of all of the microfluidic channels in the first membrane 310 do not align with the openings of the microfluidic channels in the second membrane 320, a number of such openings will align depending on the density of microfluidic channels in each of the two membranes.

The opposite surface of the second membrane 320 is placed in contact with a third membrane 330 containing microfluidic channels. The microfluidic channels of the third membrane 330 are larger in diameter than the microfluidic channels of the second membrane 320. The microfluidic channels of the third membrane 330 may approximate the diameter of the microfluidic channels in the first membrane 310 or they may be substantially smaller or larger, as long as they are not smaller than the microfluidic channels of the second membrane 320.

The area designated as cross-section A in FIG. 3 is depicted in FIG. 4. Arrows represent the flow of fluid through the adjoining membrane layers. According to Bernoulli's principle, assuming the changes in elevation, work and heat transfer are negligible, an increase in fluid velocity occurs simultaneously with decrease in pressure. Accordingly, a fluid passing through a constriction is subject to changes in velocity and pressure. In this way, a venturi speeds the flow of the fluid by constricting it in a cone-shaped tube.

Referring now to FIG. 5, a three-layer configuration approximating a venturi is shown. Liquid enters the first membrane 510 at a first velocity (V1) and a first pressure (P1). In order for any fluid flow to occur into the microfluidic channel of membrane 510, fluid must be drawn into the channel, either because the exit pressure at the end of the tube, more specifically at the outlet end 504 of the microfluidic channel in the third membrane 530, is lower than the entry pressure P1, or because liquid is drawn into the channel through capillary action. In either case, the lower pressure at the entry causes the fluid to accelerate from the intake microfluidic channel in membrane 510 into the smaller microfluidic channel in membrane 520. The smaller area, called the vena contracta, in the microfluidic channel of the second membrane 520 causes an increase in velocity and a non-recoverable decrease in pressure at the microfluidic channel outlet 503. Because the pressure drop in the larger microfluidic channel in the third membrane 530 is non-recoverable, the fluid exits the third membrane 530 at a higher outlet velocity (V2) than the inlet velocity V1.

As previously mentioned, fluid may be drawn into the microfluidic channel through capillary action. Accordingly, the membrane material should have a capillary structure and is preferably a porous material. Exemplary membrane materials include fibrous materials, ceramics and porous plastics such as that manufactured by Porex in Atlanta, Ga. Additionally, the membrane may also include a number of plastic tubes which run from one surface of the membrane to the other. Exemplary membrane materials include reticulated foam, which may range from hydrophilic, which may be used with water based liquids, to hydrophobic, which may be used with non-water based liquids.

Figure 6:
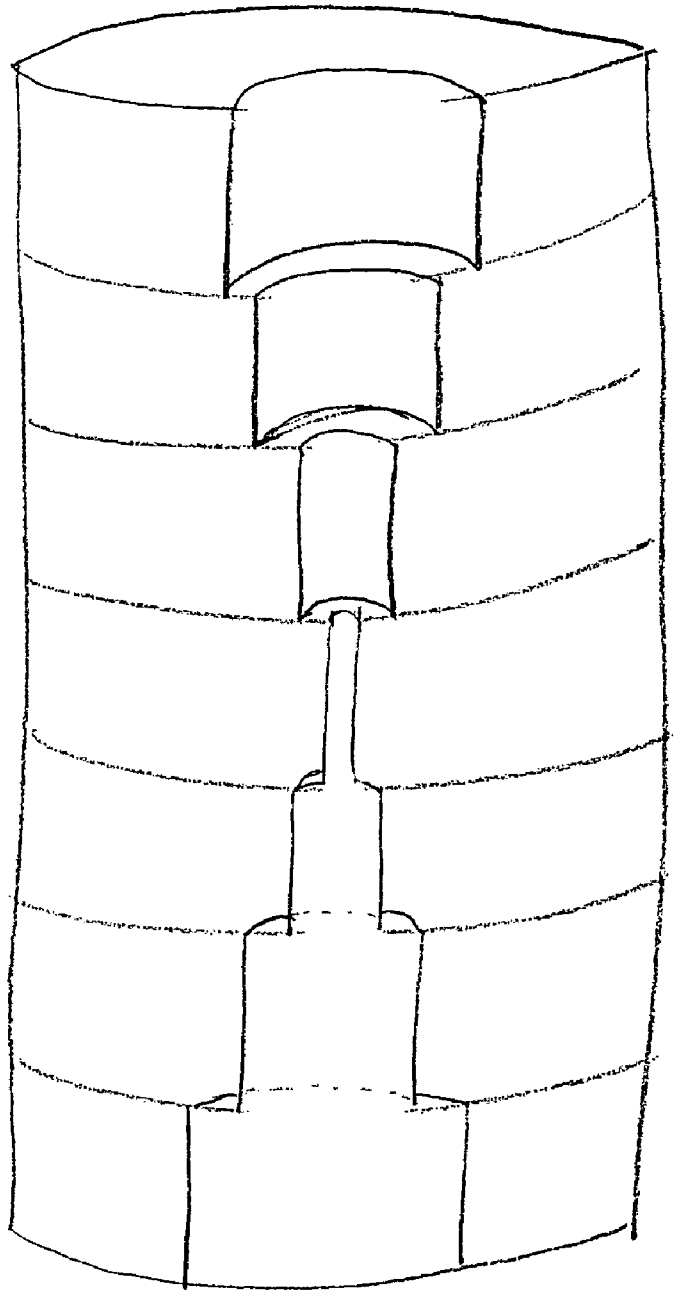
FIG. 6 shows one embodiment of the current invention in which seven membranes are interposed upon one another to approximate a venturi configuration.

Although the membrane layers described above may be, in some cases, a single piece structure, they are also contemplated as an aggregation of two or more separate layers which, when appropriately mated or joined together, form the structure described herein. In a typical configuration, the configuration of the channels through the aggregate structure will approximate a venturi. It will be apparent to those skilled in the art that, by increasing the number of layers, it is possible to better approximate the shape of a venturi. An example of a venturi with seven layers is depicted in FIG. 6.

Figure 7:
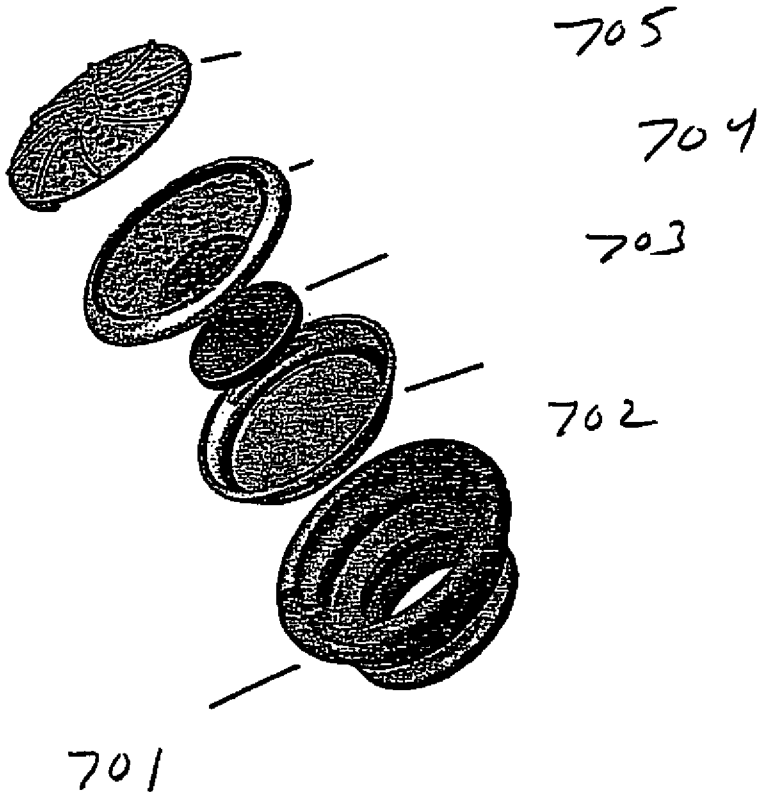
FIG. 7 shows a device incorporating one embodiment of the membrane configuration of the present invention.

The foregoing membrane structures can be employed in a number of different configurations to provide a device which can be set up and operated in a particularly simple manner. One embodiment of such a device is depicted in FIG. 7. A mounting device 701 is attached to a liquid reservoir 702 which may be filled with a solution containing an active ingredient and a base. The membrane or membrane structure 703 is placed in the liquid reservoir 702 and is covered with a housing 704. The housing 704 is covered with a cap 705 which prevents the dissipation of the solution. When the user desires to dissipate the solution, the cap 705 is either rotated so as to align holes in the cap 705 with holes in the housing 704 or, alternatively, the cap 705 may be removed entirely. Thereafter, the membrane structure 703 allows the solution to dissipate at the desired rate. Preferably, the entire device has fluid-tight seals at all interfaces between the parts thereof.

Figure 8:
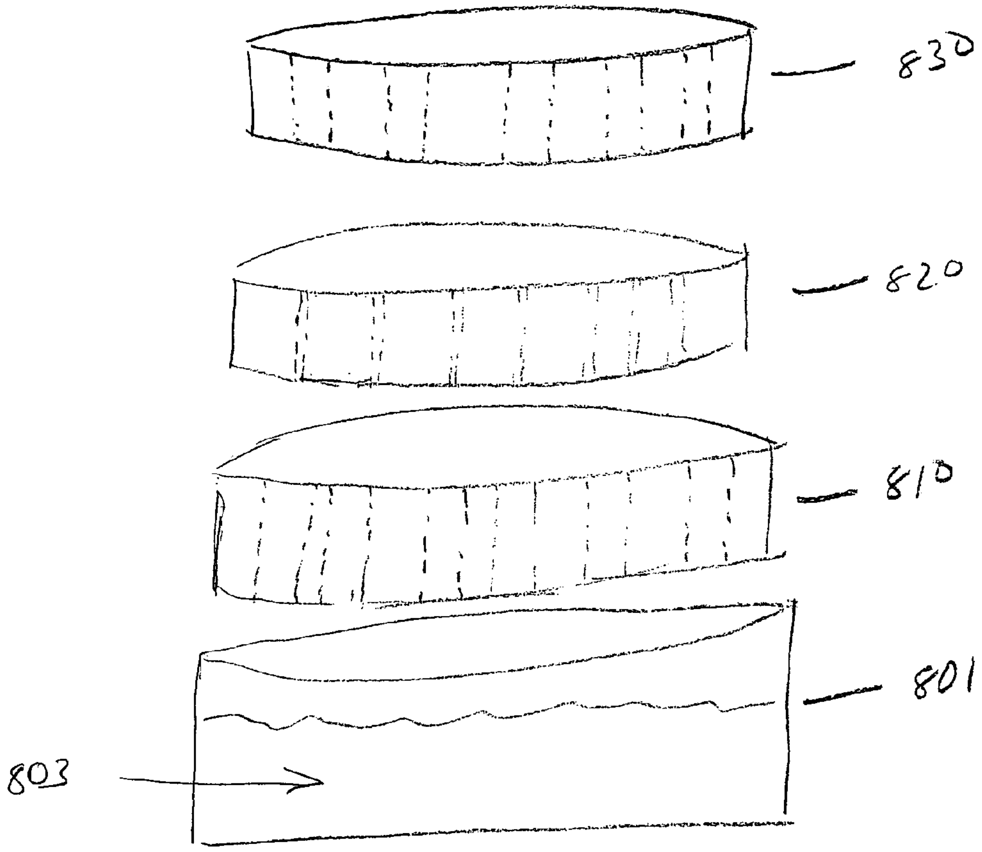
FIG. 8 shows an alternative implementation of one embodiment of the present invention.
Figure 9:
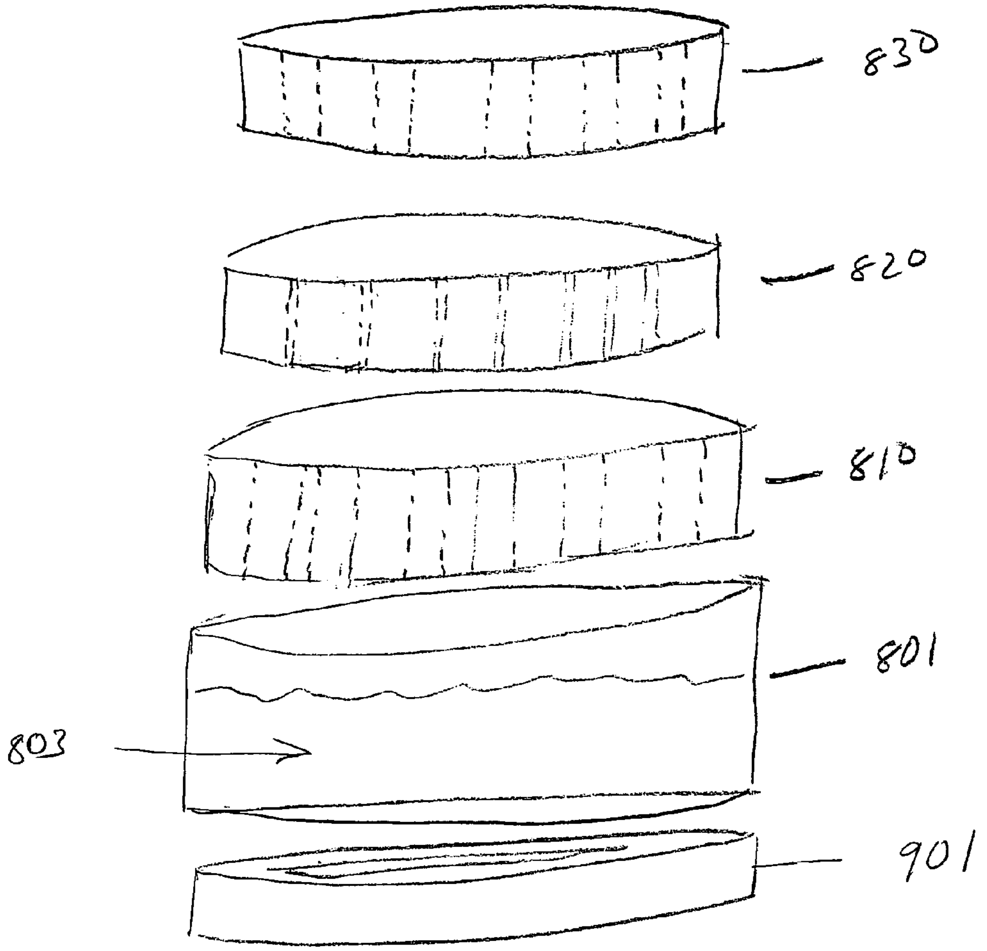
FIG. 9 shows another alternative implementation of one embodiment of the present invention.

Another configuration in which the foregoing principles can be incorporated is depicted in FIG. 8. A solution 803 is placed in a liquid reservoir 801. Membrane layers 810, 820 and 830 are configured so as to create a structure whereby a membrane 820 with a smaller microfluidic channel is interposed between two membranes 810 and 830 with larger microfluidic channels, thereby creating the venturi configuration described above. In one embodiment, heat is applied to the top of the top membrane 830 so as to accelerate the rate at which liquid leaves the microfluidic channels in the top membrane 830. In another embodiment, heat, either in the form of sensible heat or a voltage differential, is applied to the liquid reservoir 801 so as to accelerate the rate at which the solution is drawn into the microfluidic channels in the first membrane 810. For example, a heater 901 as shown in FIG. 9, such as a heater made of Kapton made by the Minco Products in Minneapolis, Minn., may be used to generate heat within the liquid reservoir 801.

There are a number of applications for the device described herein. For example, the device may be attached to a cellular phone whereupon the user is exposed to a fragrance when using the phone. Alternatively, the device may be attached to or incorporated into jewelry, such as a watch, bracelet, necklace or the like, whereupon the wearer may be exposed to a fragrance when the jewelry article is in proximity to the wearer's nose.

There are numerous additional varieties of membrane/liquid configurations and carrier devices other than those described herein that may achieve the desired result. The specific membrane/liquid configurations and carrier devices described herein are not meant to be limiting and are meant only to serve as examples of the types of configurations and devices that may be used in connection with the present invention.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of possible fluid/membrane combinations and carrier devices, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

What is claimed is:

1. A membrane used in dispersing a solution comprising:

a first membrane layer having microfluidic channels of a first average diameter;

a second membrane layer having microfluidic channels of a second average diameter;

a third membrane layer having microfluidic channels of approximately said first average diameter;

wherein said first membrane layer, said second membrane layer and said third membrane layer are superimposed together to form a single structure with said second membrane layer between said first membrane layer and said third membrane layer; and said average diameters of said microfluidic channels of said first membrane layer and said third membrane layer are larger than said average diameter of said microfluidic channel of said second membrane layer.

2. The membrane of claim 1 wherein said membrane is made of ceramic, porous plastic, reticulated foam or any combination thereof.

* * * * *